US006205455B1

(12) United States Patent
Umen et al.

(10) Patent No.: US 6,205,455 B1
(45) Date of Patent: *Mar. 20, 2001

(54) DRUG DOCUMENT PRODUCTION SYSTEM

(75) Inventors: Michael J. Umen, Glenside; Kathy J. Nomides, Sellersville; Phillip C. Wilson, Philadelphia; Erik A. Martin, Huntingdon Valley, all of PA (US)

(73) Assignee: Michael Umen & Co., Inc., Glenside, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/351,848

(22) Filed: Jul. 13, 1999

Related U.S. Application Data

(63) Continuation of application No. 09/048,744, filed on Mar. 26, 1998, now Pat. No. 5,963,967, which is a continuation of application No. 08/430,519, filed on Apr. 27, 1995, now Pat. No. 5,734,883.

(51) Int. Cl.[7] .............................. G06F 17/30; G06F 17/22
(52) U.S. Cl. .............................................. 707/513; 707/1
(58) Field of Search ................................... 707/1, 3, 104, 707/511, 531, 513

(56) References Cited

U.S. PATENT DOCUMENTS

| 4,992,939 | 2/1991 | Tyler . | |
|---|---|---|---|
| 5,148,366 | 9/1992 | Buchanan et al. | 364/419 |
| 5,267,155 | 11/1993 | Buchanan et al. | 364/419.14 |
| 5,272,623 | 12/1993 | Grubb et al. | 717/1 |
| 5,369,763 | 11/1994 | Biles | 707/3 |
| 5,655,130 * | 8/1997 | Dodge et al. | 707/511 |

FOREIGN PATENT DOCUMENTS 2150765    6/1995  (CA) .

OTHER PUBLICATIONS

"Documentum Market Application Profile" (advertisement), Documentum, Inc. No Date.

Marell, Per. "Pharmaceutical Document Management" (Presentation Slides), PharmaSoft AB, Feb. 12–15, 1995.

Marr, Andrew P. "SGML—The Business Perspective" (Presentation Slides) Glaxo Research & Development Ltd., Feb. 12–15, 1995.

Schmuff, Norman R. "The Standards—Based CMC CANDA Project—Background" (Presentation Slides), Food and Drug Administration, Feb. 14–15, 1994.

Hamphshire, N "dbPublisher," EXE, v4, n4, p.24(4), Sep. 1989.

"Black and Veatch selects Documentation as corporate document management standard; largest U.S. engineering and design firm implements Documentum to increase competitive advantage in worldwide market." Business Wire, p. 12061100, Dec. 6, 1994.

Walter, M. "Documentum: open approach to automating workflow and management of long documents" Seybold Report on Publishing Systems, v23, n7, p.3(11), Dec. 1, 1993.

(List continued on next page.)

Primary Examiner—Jack Choules
(74) Attorney, Agent, or Firm—Dann, Dorfman, Herrell & Skillman, P.C.

(57) ABSTRACT

A document production system is provided for preparing documents and managing a database of information pertaining to investigational studies of medical products. The document production system includes a data management user interface for providing user access to the database and for retrieving information from the database as specified by selected document templates for placement into word processor-compatible documents. Additionally, the data management user interface is capable of updating information stored within the database in accordance with information specified within a previously-prepared document.

4 Claims, 7 Drawing Sheets

OTHER PUBLICATIONS

Pallatto, J. "Software design tool gets new module," PC Week, v5, n41, p. 24, Oct. 10, 1988.

Brenesal, B "Q & A 4.0: the tradition continues" P.C. Sources, v2, n10, p. 361, Oct. 1991.

Schetti, S. et al., "SGML is Here to Stay" Publish, vol. 9, No. 6, p.71–78, Jun. 1994.

Dyson, E., "SFQL: When Structure Counts" RElease 1.0, vol. 91, No. 4, p.14(5), Apr. 1991.

"SGML Primer: What every Software Company Should Know about SGML." RELease 1.0, vol. 91, No. 7, p.7(7), Jul. 1991.

"Accurate Information & Ontos", RELease 1.0, vol. 91, No. 7, pp23(2), Jul. 1991.

Seymour, F. "Forms Software: Next Hot Category" PC Magazine, vol. 7, No. 16, pp77(2), Sep. 1988.

* cited by examiner

```
Clinical Study Information
                              55a
Drug Name: _____
Indication: _____     55b
Study ID:  _____

Directory for Study Documents: _____
```

```
Detail Entry: General Protocol Information

Drug Name: [DRUG NAME]
Indication: [INDICATION]
              ← 59a
Protocol #: _____
Title     : _____

Sponsor Name   : _____
Sponsor Address: _____
        City: _____     ST: _____    ZIP/CNTRY: _____
                                 ↖ 59b Completion Status: [Complete/Incomplete]
Starting Date: _____
Location: _____        ← 59c
# of Investigators: _____
Design:
  [multi-center/single-center]
  [parallel-group/crossover]      ← 61
  [single-blind/double-blind/open-label]
  [other: _____]

Treatment Group        Dose
[Group]                [Dose]
[Group]                [Dose]
[Group]                [Dose]
           ↖ 59d
```

Tab between windows; Alt-I Investigators; F7 when done

FIG. 5

```
Detail Entry: Results   Drug: [DRUG NAME]
                        Protocol: [#]

Duration: _____    60a
                    ↵
                                    Age    Mean   %    %
                   Group    Dose    Range  Age   M/F  B/W/O
                        60b
                   [GROUP]  ↘      ___    ___   ___  ___  ___
                   [GROUP]         ___    ___   ___  ___  ___
                   [GROUP]         ___    ___   ___  ___  ___
```

FIG. 6

DRUG DOCUMENT PRODUCTION SYSTEM

RELATED APPLICATIONS

This application is a continuation of application Ser. No. 09/048,744, entitled "Drug Document Production System," filed on Mar. 26, 1998, now U.S. Pat. No. 5,963,967, which in turn is a continuation of application Ser. No. 08/430,519, filed on Apr. 27, 1995, now U.S. Pat. No. 5,734,883, such applications being incorporated herein by reference.

FIELD OF THE INVENTION

The present invention relates to a method and system for structured composition of drug documents and, more particularly, to an automated method and system for assisting an author in composing the contents of drug documents and for organizing the contents within a computer data storage system, and for retrieving the contents from the data storage system to produce drug documents in any of various selected formats.

BACKGROUND OF THE INVENTION

Before a new drug, biological agent, therapeutic device or other potentially therapeutic substance or treatment is marketed or practiced in a particular country, the approval of a government authority is often required. In the United States, for example, the authority to approve the use or sale of new drugs is vested in the Food and Drug Administration (FDA). pursuant to the Federal Food, Drug and Cosmetic (FD&C) Act. "Drugs" are defined as "articles intended for use in the diagnosis, cure, mitigation, treatment or prevention of disease in man" and "articles (other than food) intended to affect the structure or any function of the body of man."

The general procedure for introducing a new drug in the United States begins with the discovery or synthesis of the drug, or a determination that a previously-known drug may have a new therapeutic use. If the clinical safety of the drug is not known on the basis of existing data, pre-clinical short-term animal studies may be undertaken to develop a pharmacological profile of the drug and to determine the toxicity of the drug. When the reasonable safety of the drug is established, the relevant data is then submitted to the FDA in an Investigational New Drug (IND) Application. The IND also includes a proposal for determining the safety and efficacy of the drug in clinical trials. The drug developer may then begin clinical trials if no objections are raised by the FDA upon review of the IND.

Clinical testing of a new drug may involve numerous clinical studies and may take several years to complete. Such studies are ordinarily conducted in as many as three phases. Phase I clinical studies relate to basic safety investigations of the new drug in humans. A typical Phase I clinical study is conducted with a small number of healthy volunteer subjects to whom the drug is administered. The results obtained during Phase I studies are used to determine such parameters as the toxicity, absorption, metabolism, preferred route of administration and safe dosage range of the drug. If the results from Phase I studies are favorable, the developer may proceed to Phase II studies.

In Phase II studies, the drug is administered to populations of subjects presenting the indication for which the drug is being tested. Phase II studies are used to gather additional safety data and to provide initial results relating the effectiveness of the drug.

Prior to beginning Phase III studies, the drug developer may provide data from completed or ongoing Phase I and Phase II studies to the FDA during periodic update reports or meetings. Phase III studies are undertaken in order to determine dosage, safety, and effectiveness in large populations and to develop labelling information for the drug.

At or near the conclusion of clinical testing, the developer is then ready to prepare a New Drug Application (NDA). An NDA is typically a massive document comprising several volumes of reports. Depending upon the type of drug, the NDA may include an index, a summary, and several sections relating to the chemistry, pharmacology, pharmacokinetics, clinical effects, and proposed labelling of the drug. Each one of these sections may also include several documents. For example, the clinical section of an NDA may include an index, an abbreviated clinical summary, a risk/benefit analysis, an integrated summary of effectiveness, an integrated summary of safety data, clinical pharmacology study reports, controlled study reports, uncontrolled study reports, and other information pertaining to the accumulated knowledge and experience gained during clinical testing of the drug.

Each section of an NDA includes many cross-references among complex documents that relate to studies conducted over a period of time that can extend over several years. Thus, the composition of textual descriptions of study data, and the integration of such text into a consistent NDA can be a complex and time-consuming process. Once completed, the NDA is sent to the FDA for their review. The length of time required by the FDA to review an NDA is highly dependent upon the degree to which the NDA is well-organized, consistent, complete, and in compliance with the governing regulations and guidelines. Additionally, further documentation may be required in connection with clinical studies undertaken after submission of the NDA, or after approval of the drug.

The prescribed format and contents of an NDA are, of course, only suitable for obtaining review by the United States FDA. In order to obtain approval of the drug in other countries, essentially the same data may be required to be submitted to the respective governing authorities in each of the desired countries. For example, if it is also desired to market the new drug in Europe, then approval must be obtained from a corresponding administrative body of the European Union (EU). The EU has instituted a pre-marketing regulatory review program for new drugs that is similar to the NDA review program conducted by the FDA. Because the EU has formulated regulations for the review of new drugs that are in some ways different from the US regulations, the developer is burdened with the task of producing an additional set of hierarchically-related documents which rely upon the same data that was used to produce the NDA. Additionally, the developer may also desire to produce internal company reports which also present the same drug data in yet another customized format.

In the interest of reducing pre-marketing delay in the United States and abroad, it would be highly desirable to provide an automated system for managing the authoring of contents, for organizing text and details associated with drug studies into a convenient database, and for integrating such information in the form of standard documents. Such a system would also be desirable to be adapted for use in preparing documentation, such as Product License Applications or Establishment Licenses, in connection with studies relating to medical devices or to biological agents, such as viruses, sera, toxins, antitoxins, and the like. It would also be desirable to provide such a system that would be adapted to arranging such information in the form of documents that are compliant with each of the various manners which may be prescribed for such documents by U.S. or foreign regulatory agencies, or as desired by the developer.

SUMMARY OF THE INVENTION

In accordance with the present invention, there is provided a computer-implemented document production system for managing the composition of textual information pertaining to studies of a medical product, such as a drug, a biologic, or medical device; for storing drug information within a computer data storage and retrieval system; and for organizing such information in order to generate drug documents according to predetermined document formats. The documentation system includes a computer having a word processing system; a data storage and retrieval system accessible to the computer; a data management user interface (DMUI) installed within the memory of the computer; and a plurality of document templates each for specifying the arrangement of information within a particular type of document to be generated. The data management user interface provides the computer with the ability to guide a user to compose and to effect entry of textual medical product information into the data storage and retrieval system, to effect generation of documents on the basis of the stored data and the document templates, and to provide helpful guidance to the user in composing the text objects to be utilized in producing a document. The documents that are generated are compatible with the word processing system for further refinement, editing, or printing of the generated documents. The data storage and retrieval system can also be operated via the DMUI to effect the storage of medical product data therein on the basis of information that is automatically collected from previously-generated documents.

According to another aspect of the invention, there is provided a documentation system wherein a computer is arranged to generate pre-defined medical product documents on the basis of information stored within a medical product information database and wherein the information within the database can be updated by the computer on the basis of information contained within pre-defined documents. Hence, a collection of hierarchically-related documents can be produced while at the same time providing the ability for any changes made to a relatively higher-level document to be reflected in the lower-level documents or in the raw data contained within the information database.

BRIEF DESCRIPTION OF THE DRAWINGS

The foregoing summary, as well as the following detailed description, will be best understood in conjunction with the attached drawings in which:

FIGS. 4–6 show views of interactive forms generated by the data management user interface of FIG. 3 and displayed upon a computer display device for allowing an operator to enter information into a clinical study database within the computer of the drug document production system.

DETAILED DESCRIPTION

The present invention provides an automated system for composing and generating hierarchically-related documentation that is desired in connection with studies of medical products such as drugs, biological agents, or medical devices. As used herein, the term "drugs" shall refer to any of these aforementioned medical products.

Figure 1:
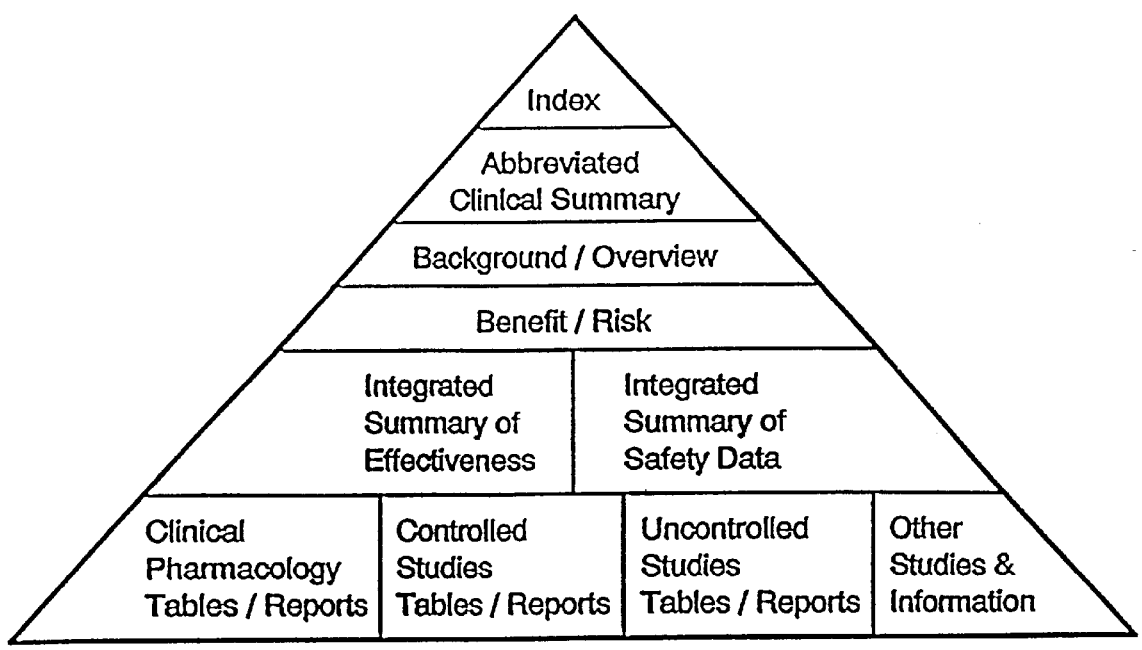
FIG. 1 is a diagram of a hierarchy of documents that are submitted in a clinical section of a New Drug Application.

The hierarchically-related documents which constitute each section of a New Drug Application (NDA) are examples of the types of documentation that are desirable to be produced in connection with drug studies. For example, the hierarchical relationships among the documents of the clinical section of the NDA are generally structured as shown in FIG. 1. At the bottom of the clinical section hierarchy are the individual study reports pertaining to each of the clinical studies. Selected data, results, and other information from the individual studies are incorporated into the respective integrated summaries of effectiveness and safety. Information from the integrated summaries is, in turn, utilized in the risk/benefit analysis, and so on.

Figure 2:
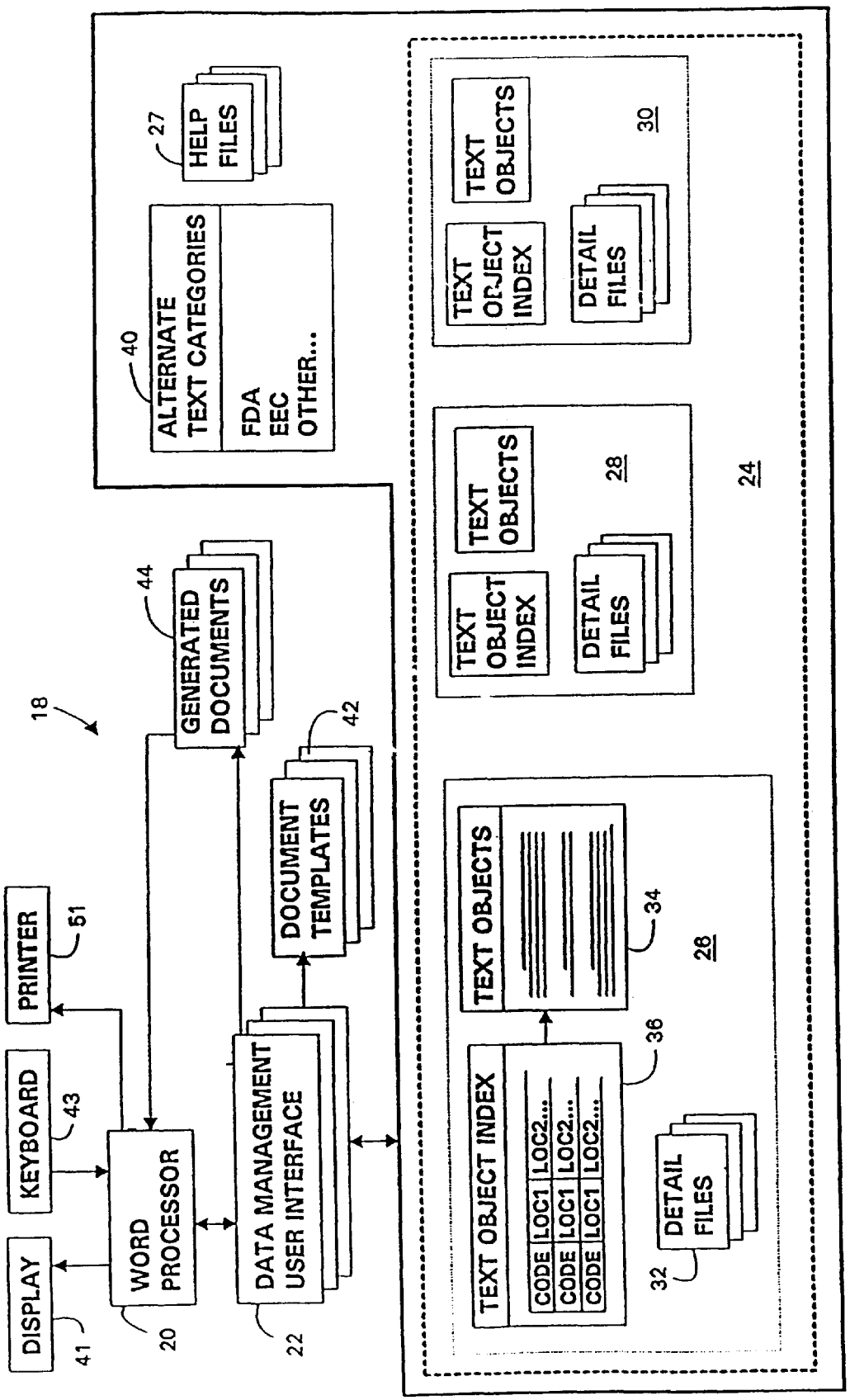
FIG. 2 is a functional block diagram of a computer-aided drug document production system;.

The drug document production system, generally designated 18, is organized as shown in FIG. 2. In the preferred embodiment, the various functional components of the system 18 are implemented by a personal computer and associated peripheral equipment, such as a display-device 41 for displaying information to the user, a keyboard 43 for allowing the user to enter textual information, and a printer 51 for printing documents. A word processor 20 is operatively installed within the memory of the computer for providing the primary user interface to the drug document production system. The word processor 20 may include a commercially-available word processing system, such as the popular WORDPERFECT word processing system. The word processor 20 provides the user with the ability to perform a variety of editing functions upon text stored within the computer and to effect the printing of documents via the printer 51. Preferably, the word processor 20 is of a type that allows the user to enter user-defined codes into a document that do not form a part of the printed document. In the WORDPERFECT system, for example, the electronic version of a document may contain control codes which are used to signal that the appearance or format of portions of text are to be displayed or printed differently than other portions of text. Additionally, the WORDPERFECT system provides additional codes which are not used by the word processor, but which can be defined by the user to cause the computer to perform customized functions. Such a provision for user-defined control codes is also provided in other commercially-available word processing systems. In the drug documentation system 18, such user-defined control codes are used within drug documents to delimit -data fields within the documents, and to indicate the-types of data objects which are to be inserted into the delimited fields during data retrieval and document generation.

A data storage and retrieval system 23 is provided for organizing drug information that is to be incorporated into selected drug documents. For example, a clinical study database 24 is included in the data storage and retrieval system 23 for organizing data pertaining to clinical trials of drugs under development. Other databases may also be used and may have some fields in common with the clinical study database. For example, for non-clinical studies or reports, a non-clinical database would be used. The data storage and retrieval system 23 is preferably implemented as a collection of files stored within a read/write mass data storage device, such as a hard disk system of a personal computer. Executive components of the document production system 18, such as the word processor 20 and a data management user interface 22, may also reside within the hard disk system and be loaded into random-access memory of the computer for execution. Operation of the document production system 18 involves functional interaction of the executive components of the document production system 18 with the data storage and retrieval system and with the user via the display 41, keyboard 43, or printer 51.

Access to the data storage and retrieval system 23 from within the word processor 20 is provided by the data management user interface 22 (DMUI). The data management user interface 22 includes procedures for manipulating information within the data storage and retrieval system 23, for integrating clinical study data into pre-defined document templates 42 in. order to generate drug documents 44 that are compatible with the word processor 20, and for generating interactive displays upon the display device 41 to prompt an operator to compose text via the keyboard 43 and/or to allow the user to selectively activate various other functions of the DMUI 22.

The drug documentation system begins execution by loading the data management user interface 22 into memory of a computer and then invoking execution of the word processor 20 by the computer. The data management user interface 22 preferably remains loaded in the memory of the computer while the word processor is in operation. Such operation of the DMUI 22 is known in the art as a "terminate and stay resident" (TSR) mode of operation. The word processor 20 is preferably of the type which allows selective activation of TSR programs upon actuation of a pre-selected control key of the keyboard 43 by the user. In embodiments employing the popular WORDPERFECT word processor, the various menus and function keys used by the DMUI 22 are preferably designed to be consistent with the types of menus and function keys that are ordinarily utilized during execution of WORDPERFECT. Thus, to the user, the DMUI can be made to appear as an enhanced feature of the word processor 20.

The DMUI 22 is preferably menu-driven, so that only a minimum of special knowledge is required to operate the. DMUI 22 other than basic computer skills and familiarity with the preferred word processor 20. The menus provided by the DMUI 22 can be generated and displayed upon the display device 41 in accordance with well-known techniques for providing selective activation of programmed operational modules or procedures of a computer system. Alternatively, or in addition thereto, the DMUI may provide a graphical user interface to the respective procedural modules of the system 18.

Figure 3:
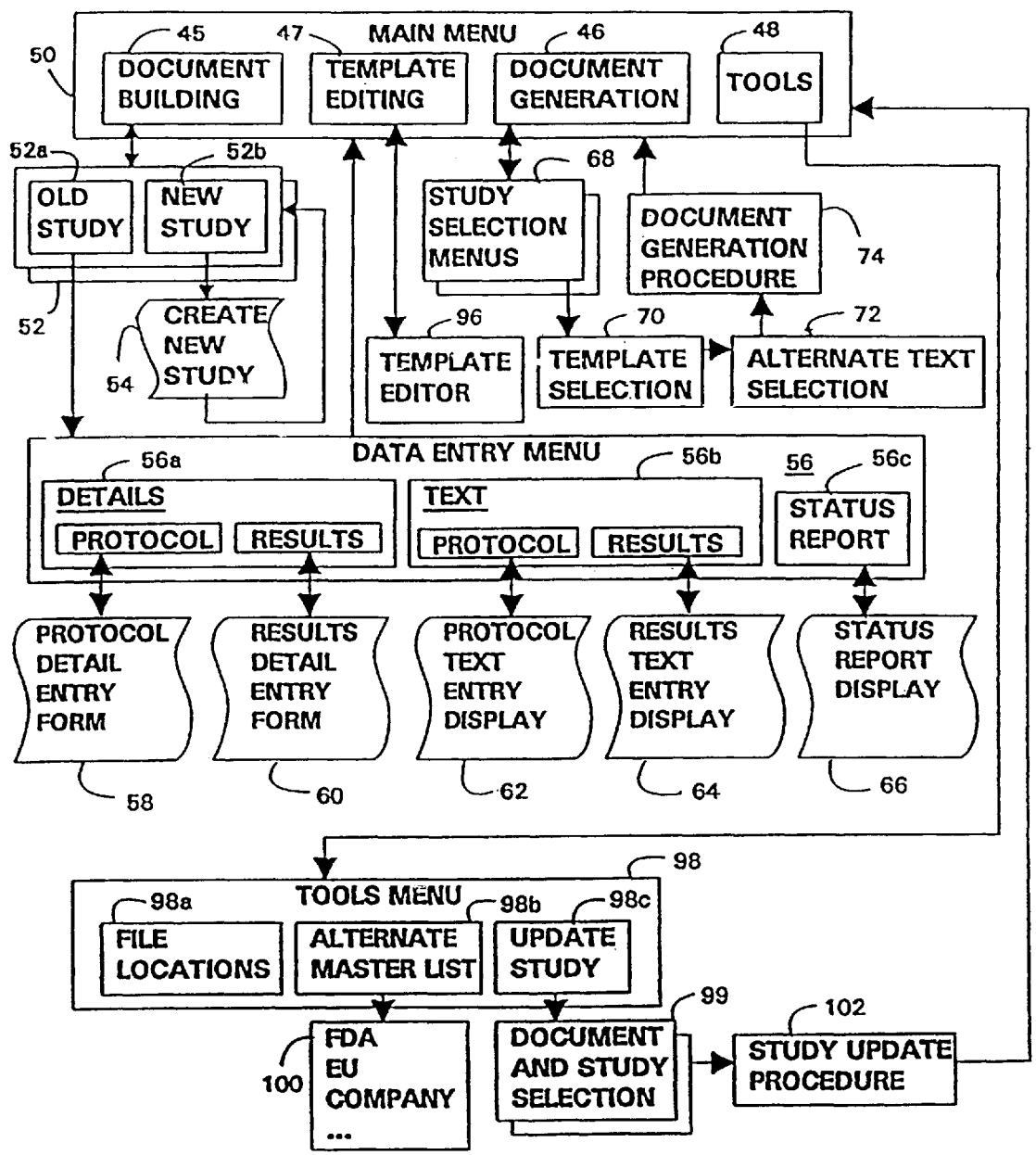
FIG. 3 is a procedural flow diagram of functions performed within the computer by a data management user interface of the drug document production system of FIG. 2.

Referring now to FIG. 3, there is shown a tree diagram of the menus and interactive worksheets that are generated and displayed by the DMUI. Upon activation of the DMUI from within the word processor, a main menu 50 provides four procedural selections designated "Document Building", "Document Generation", "Template Editing", and "Tools." The Document Building selection 45 causes the computer to execute procedures for entering or editing text or detail objects associated with a clinical study in the clinical study database. The Document Generation selection 46 causes the computer to execute procedures for arranging the clinical study data into predefined document templates. The Template Editing option 47 provides for execution of procedures for editing document templates and for defining new templates. The Tools selection 48 provides for execution of procedures for setting. default directory paths for files used by the drug documentation system, for defining categories of certain data objects, and for entering study data into the clinical study database from a previously-generated document. Each of the procedural modules that can be activated by the user from the main menu 50 is described in greater detail hereinbelow. It shall be apparent that the groupings of procedural modules as options under the various menus of the. DMUI can be altered as desired.

DOCUMENT BUILDING/DATA ENTRY

When Document Building 45 is selected, the DMUI 22 displays one or more menus 52 upon the display device 41 for prompting the user to select an existing study 52a or for allowing the user to indicate that a new study 52b is to be added to the clinical study database. If the user chooses to create a new study 52b, then the DMUI proceeds to produce and display an interactive study creation form 54, which is shown in greater detail in FIG. 4. The study creation form 54 includes data entry fields 55a,b for entering the name of the drug to be studied, the indication for which the drug is to be tested, a study identification code, and a directory path for study documents. The study identification code is a unique identifier such as a protocol number, an internal cataloging number, or other item which uniquely identifies the drug and the study. When the user has completed the study creation form 54, then an appropriate key is pressed to signify completion of the form 54 and to instruct the DMUI 22 to create a new study entry in the clinical study database 24.

Referring again to FIG. 2, the clinical study database 24 may contain several study entries 26, 28, and 30. Each study entry in the database, for example study entry 26, is implemented as one or more detail files 32 and at least one text object file 34 stored within the preferred data storage device of the computer. Additionally, the study entry 26 includes a text object index 36, which includes a pointer table for locating text objects within the text object file 34. The DMUI 22 is programmed to organize the clinical database 24 by using the study identification code as the first part of each filename within a study entry, followed by an extension identifying the type of file.

The detail files 32 are used to store relatively small data objects, designated herein as study details., that are typically used often within a drug document or are common to many documents in an NDA. Study details include the name of the drug, the location of the study, the completion status of the study, and other information that may be expressed in a single word, number, or short phrase. A more comprehensive list of representative study details is shown in TABLE 1A and 1B.

The text object file(s) 34, as shown in FIG. 2, is used for storing more extensive data items, referred to hereinafter as "text objects," that are associated with a clinical study. For example, text objects may include a statement of the objective of the study, conclusions reached during the study, criteria for patient inclusion or exclusion, and other categories of study information that can be characterized as text of as much as, for example, a sentence, several sentences, or several paragraphs. Graphic images or statistical tables, in the form of respective standard graphical or statistical format files, may also be included among the text objects that are stored in connection with a study entry. The DMUI may be provided with appropriate routines for operating the computer to retrieve and display or print graphic images in such standard formats as TIFF, PCX, EPS, and the like. Additionally, the text object file may include further pointers to such items as statistical data in the format prescribed by Statistical Analysis Systems (SAS) Institute specifications or text objects located in various standard database formats. A more comprehensive list of representative text objects is shown in TABLE 2A, 2B, 2C and 2D.

Referring again to FIG. 3, after the user has created a study entry, then the DMUI 22 returns to menu 52. From menu 52, the user may return to the main menu 50 or may select an existing clinical study 52a and then proceed to data entry menu 56 in order to enter or edit clinical study data in the clinical study database 24. Within the data entry menu 56, the user is provided with options that include entering or editing study details, entering or editing study text objects, or ascertaining the status of a study. Upon selecting the Details option 56a from menu 56, the user is provided with a choice of editing Protocol Details or Results Details. If the user selects Protocol Details, then the DMUI proceeds to generate and display interactive protocol form 58. If the user selects Results Details, then the DMUI proceeds to generate and display interactive results form 60.

Interactive protocol form 58 is provided as a computer-generated display by the DMUI for displaying details pertaining to a clinical study protocol and for allowing the user to enter values for the protocol details into the clinical study database 24. As shown in FIG. 5, the interactive protocol form 58 includes data entry fields 59a–d for the Protocol Number, the Protocol Title, the Sponsor Name, the Sponsor Address, the Completion Status of the study, the Starting Date, the Number of Investigators, and a list of Treatment Groups and Doses given to each treatment group. A Design portion of the protocol detail entry form 58 includes a submenu 61 by which the user may select any combination of study designs such as multi-center/single-center, parallel-group/crossover, single-blind/double-blind/open-label, or a user-specified experimental design. An additional submenu, e.g. as selected by the ALT-I entry, allows the user to specify Investigators and Institutional Affiliations of the investigators. When the user has completed the protocol detail entry form 58, then the DMUI enters the protocol details into detail files associated with the selected study entry in the clinical study database. Alternatively, the user may specify that the requested details are already located within a data structure elsewhere within a data storage and retrieval system accessible to the computer, for example, in an SAS statistical output file. In such an instance, the DMUI will store within each affected detail file, a pointer for indicating the location of the pre-existing SAS data within a storage device connected with the computer. Similarly, the DMUI may be provided with executable modules for accessing data in various respective database formats. For example, the DMUI may be provided with the ability to store pointers to details or text that are located within commercially available database formats. The user may then return to the data entry menu 56.

Interactive Results Details Entry form 60, as shown in FIG. 3, is provided as a computer-generated display by the DMUI for displaying details pertaining to the results of a clinical study and for allowing the user to enter values for the results details into the clinical study database 24. As shown in FIG. 6, the Results Details Entry form 60 provides data entry fields 60a,b for entering the Duration of Treatment and the Dose, Age Range, Age Mean, Male/Female percentage, and Racial Composition of each of the treatment groups that were specified during entry of the protocol details. When the user has completed the Results Details Entry form 60, then the DMUI enters the results details into the detail files associated with the selected study entry in the clinical study database. The user may then return to menu 56,.

Within the menu 56, the user may select to enter text objects associated with either the protocol or the results associated with a study. Upon selecting to enter protocol text 56b, the DMUI provides an interactive worksheet 62 as a computer-generated display for entering text objects pertaining to the protocol of the study. Such text objects may include an Introduction, the Objective, the Investigational Plan, the Study Design, and other text objects that are associated with a selected clinical study protocol. The interactive worksheet identifies each of the text objects, and the user then enters the requisite text beneath the identification of each text object. The text object entry worksheet 62 functions in a manner that is similar to the word processor, and the implementation of the worksheet may cause the computer to activate selected functional modules of the word processing system to provide the text entry and manipulation features of the worksheet 62. Additional features of the text object entry worksheet 62 may also be provided. For example, the DMUI 22 may present the text object entry worksheet to the user as a "split-screen" display. In one portion of the screen, the DMUI may display section headings, or other indicia of the requisite text objects, and a movable cursor. As the user positions a cursor within areas of the worksheet 62 associated with various text objects, the DMUI generates, within another portion of the screen, a display of instructions, advice, or other information that would be helpful to the user in composing the indicated text object. In order to provide such helpful information, the data storage and retrieval system is provided with a plurality of help files 27 wherein each help file is used to store helpful information pertaining to a particular type text object. Thus, when the user locates the cursor in an area of the screen associated with a particular text object, the DMUI retrieves the contents of the associated help file and displays such contents in a designated portion of the screen.

Because the study details and the text objects are stored within separate detail files and text object files for each study entry in the clinical study database, the user can include embedded references to study details within any of the text objects. In order to produce such embedded references, the interactive worksheet 62 may respond to operation of a predetermined function key for placing into a text object an electronic code representing a reference to a study detail. Upon activation of such a key, the interactive worksheet 62 may display a menu of study details from which the user may select a detail for placement as a coded reference into the text object being entered. Alternatively, a corresponding function key or key combination may be assigned to each study detail for directly entering a detail reference into a text object. For example, in order to specify the Objective of a study, the user might enter:

"The objective of this study is to determine the effectiveness of aspirin for the treatment of headaches."

or:

"The objective of this study is to determine the effectiveness of <<DRUG NAME>> for the treatment of <<INDICATION>>."

where "<<DRUG NAME>>" and "<<INDICATION>>" are predetermined coded references to the corresponding study details, e.g. the drug name and the indication, selected from the menu or directly entered via the function key. When a detail reference is embedded within a text object, the DMUI retrieves the appropriate detail from the detail files of the study entry and displays the retrieved detail within the displayed entered text in a distinct manner, such as by highlighting the retrieved detail in context to indicate that the text object contains a detail reference instead of raw text at the indicated location. If the referenced detail has not yet been entered into the detail files of the current study, then the DMUI will fail to retrieve the selected detail. In such a circumstance, an appropriate notation will be displayed at the location of the embedded reference. The user may then continue to enter additional text in the absence of a defined value of the undefined detail, since it is the coded reference to a detail that is embedded in the text object and is subsequently stored, within the text object, in the text object file, rather than the actual contents of the corresponding detail.

By allowing embedded references to study details to be placed into the text objects, the DMUI provides the user with the ability to compose generic text objects that can be imported into the text object files of any of the study entries in the clinical study database. Additionally, text objects containing embedded detail references can be copied from the text object files of a pre-existing study entry into the text object file of a later study entry, thus allowing pre-existing text objects to be reused in later-desired documents. The interactive worksheet 62 provides appropriate function keys for enabling the user to request or otherwise specify that a text object is to be copied from a pre-existing study. Any embedded details in an imported text object will then be displayed in accordance with the existing details of the current study, and the user may further edit the imported text object as desired. When the user has completed entry of the protocol text objects, or a subset thereof, the text objects, including any embedded detail reference codes, are stored within the text object file of the study entry and the user may return to menu 56. Additionally, the text object index 36 is provided with a pointer to the current locations of the entered text objects within the text object file 32 when the text object file is modified.

From menu 56b, the user may also select to enter Results Text Objects pertaining to a study entry. Entry of Results Text Objects is performed within interactive worksheet 64 in a manner similar to interactive worksheet 62, except that the text objects to be entered thereon pertain to study-result oriented information, such as statistical results, observations and conclusions. The implementing code for the interactive worksheets 62 and 64 may include portions of the implementing code of the word processor, or may include custom code for providing similar word processing functions. When the user has completed entry of the results text objects, or a subset thereof, the text objects, including any embedded detail reference codes, are stored within the text object file of the study entry and the user may return to menu 56. Additionally, rather than entering the desired text or detail objects manually via the worksheets and interactive forms described herein, the user may specify other databases from which the desired text or detail objects may be retrieved. The text object index 36 is updated to identify the current locations of each entered text object, or pointer to a text object stored elsewhere, within the text object file 32 when such text objects files are modified by the user.

The interactive text object entry worksheets 62 and 64 also provide the ability for the user to specify alternate text objects of the same type that are specific to certain forms of drug documents. For example, the study results text objects might include a discussion of a statistical analysis of the results. It may be the case that the FDA prefers one type of statistical test, while an alternative statistical test is required by the EU. Hence it would not be possible to provide a single Statistical Analysis text object that could be incorporated into drug documents prepared for the FDA and for the EU. In order to provide for entry of alternate text objects, a list of alternate text categories 40 is stored in the data storage and retrieval system 23. The entries within the alternate text category list may include such designations as "FDA", "EU", or "Company" for designating categories of alternate text objects. Then, prior to the entry of a text object into an interactive text object entry worksheet, the user may specify that the current text object is one of a plurality of alternate texts to be entered into the text object file for the current text object. The DMUI then retrieves and displays the list of alternate text categories and allows the user to specify which category of alternate text is to be associated with the currently-specified text object. In order to manage storage and retrieval of alternate text objects into the text objects file, the text object index includes a pointer table which contains for each text object index entry, a list of pointers to the location of text objects within the text object file. Each text object pointer in the list of pointers for each text object type is used by the DMUI to locate the respective alternate texts which may be found for each text object. For example, each table entry may include a text object identification code followed by a list of locations (in the order specified in the alternate text category list) within the text object file for each corresponding alternate text.

The remaining option in menu 56 is the Status Report option 56c. Upon selection of the status report option, the DMUI scans the detail files of the selected study entry and then displays a tabular list 66 of protocol and results details that have not, as yet, been entered into the detail files of the selected study entry. The status report procedure allows the user to quickly ascertain whether any necessary information is required to complete a study entry. The user may then return to menu 56.

DOCUMENT GENERATION

The Document Generation option 46 of the main menu 50 provides access to procedures for generating drug documents on the basis of pre-defined document templates and information contained within the clinical study database. Each of the document templates 42 specifies the type and order of data objects that are to be retrieved from the clinical study database in order to produce a standard drug document in accordance with FDA, EU, Company, or other predetermined document formats. Table 1 lists representative study details that may be specified within representative standard types of documents. Table 2 lists representative text objects that may be specified within representative standard types of documents. The L designation on Table 2 indicates that certain information or text objects in the main portion of a document, such as a core report section of a full integrated clinical and statistical report of a clinical study in an NDA, may be linked as hypertext, for example, to the corresponding appendices or tabulations related to the subject study. For example, text objects in the form of summary tables in the core report section of the document may be linked as hypertext to tables or images of raw data, such as individual case report forms, in an appendix.

TABLE 1A

REPRESENTATIVE DOCUMENT TYPES AND DETAILS

DOCUMENT TYPE

| Object | IDB[1] | Protocol | Full Report | Appendices | Tabulations | US Synopsis | EU Synopsis | Overview Table[4] | ISE[2,4] | ISS[3,4] |
|---|---|---|---|---|---|---|---|---|---|---|
| DETAILS |||||||||||
| Protocol Number | X | X | X | X | X | X | X | X | X | X |
| Protocol Title | X | X | X | X | X | X | X |  | X | X |
| List of Investigators | X | X | X | X |  | X | X | X | X | X |
| List of Invest. Affiliations | X | X | X |  |  |  | X |  |  |  |
| Summary of study Design | X | X | X |  |  | X | X | X | X | X |
| Completion Status |  |  |  |  |  |  |  | X | X | X |
| Treatment Groups | X | X | X |  |  | X | X | X | X | X |
| Treatment Group Dose | X |  |  |  |  |  |  | X | X | X |

TABLE 1A-continued

REPRESENTATIVE DOCUMENT TYPES AND DETAILS

DOCUMENT TYPE

| Object | IDB[1] | Protocol | Full Report | Appendices | Tabulations | US Synopsis | EU Synopsis | Overview Table[4] | ISE[2,4] | ISS[3,4] |
|---|---|---|---|---|---|---|---|---|---|---|
| Treatment Group Age Range | X | | X | | | X | | X | X | X |
| Treatment Group Mean Age | X | | X | | | X | | X | X | X |
| No. of Subjects Entered in each Treatment Group | X | | X | | | X | X | X | X | X |

[1] Investigator's Brochure
[2] Integrated Study of Effectiveness
[3] Integrated Study of Safety
[4] Multi-Study Document

TABLE 1B

REPRESENTATIVE DOCUMENT TYPES AND DETAILS

DOCUMENT TYPE

| Object | IDB[1] | Protocol | Full Report | Appendices | Tabulations | US Synopsis | EU Synopsis | Overview Table[4] | ISE[2,4] | ISS[3,4] |
|---|---|---|---|---|---|---|---|---|---|---|
| | | | | | DETAILS | | | | | |
| % Male/Female in each Treatment Group | X | | X | | | X | X | X | X | X |
| % Black/White/Other in each Treatment Group | X | | X | | | X | | X | X | X |
| Sponsor Name | X | X | X | X | X | X | X | | X | X |
| Sponsor Address | X | X | X | | | X | | | | |
| Name of Drug | X | X | X | X | X | X | | X | X | X |
| Start Date | X | | X | | | | X | X | X | X |
| End Date | X | | X | | | | X | X | | |
| Location of Study | X | | | | | | | X | X | X |
| Test Product Dose and Batch No. | | | | | | | X | | | |
| Placebo Dose and Batch No. | | | | | | | X | | | |
| Duration of Treatment | X | X | X | | | X | X | X | X | X |

[1] Investigator's Brochure
[2] Integrated Study of Effectiveness
[3] Integrated Study of Safety
[4] Multi-Study Document

TABLE 2A

REPRESENTATIVE DOCUMENT TYPES AND TEST OBJECTS

DOCUMENT TYPE

| Object | IDB | Protocol | Full Report | Appendices | Tabulations | US Synopsis | EU Synopsis | Overview Table | ISE | ISS |
|---|---|---|---|---|---|---|---|---|---|---|
| | | | | | TEST OBJECTS | | | | | |
| PROTOCOL ORIENTED TEST OBJECTS | | | | | | | | | | |
| Introduction | X | X | X | | | | | | | |
| Objective | X | X | X | | | X | X | | X | X |

TABLE 2A-continued

REPRESENTATIVE DOCUMENT TYPES AND TEST OBJECTS

| | | | | | | DOCUMENT TYPE | | | | |
|---|---|---|---|---|---|---|---|---|---|---|
| Object | IDB | Protocol | Full Report | Appendices | Tabulations | US Synopsis | EU Synopsis | Overview Table | ISE | ISS |
| Study Design | X | X | X | | | X | X | | X | X |
| Treatments | | X | X | | | X | | | X | X |
| Inclusion Criteria | X | X | X | | | | X | | | |
| Rejection Criteria | X | X | X | | | | | | | |
| Patient Samples | X | X | X | | | | X | | | |
| Informed Consent | X | X | X | | | | | | | |
| Study Population | X | X | X | | | | | | | |
| Methods of Assigning Patients to Treatment | X | X | X | $L^5$ | | | | | | |
| Dose Selection | X | X | X | | | | | | | |
| Blinding | X | X | X | | | | | | | |
| Criteria of Effectiveness | X | X | X | | | | X | | | |
| Criteria of Safety | X | X | X | | | | | | | |
| Concomitant Therapy | X | X | X | | | | | | | |
| Description and Timing of Study Procedures | X | X | X | | | | | | | |

[5]Hypertext Link to Raw Data or Form Images

TABLE 2B

REPRESENTATIVE DOCUMENT TYPES AND TEST OBJECTS

| | | | | | | DOCUMENT TYPE | | | | |
|---|---|---|---|---|---|---|---|---|---|---|
| Object | IDB | Protocol | Full Report | Appendices | Tabulations | US Synopsis | EU Synopsis | Overview Table | ISE | ISS |

TEST OBJECTS

PROTOCOL ORIENTED TEST OBJECTS

| | | | | | | | | | | |
|---|---|---|---|---|---|---|---|---|---|---|
| Flow Chart of Study Procedures | X | X | X | | | | | | | |
| Removal of Patients From the Study | X | X | X | | | | | | | |
| Packaging/Labeling/ Distribution/Administration | X | X | X | | | | | | | |
| Other Supplies | X | X | X | | | | | | | |
| Criteria for Inclusion in Evaluable Data Set | X | X | X | | | | | | | |
| Planned Analysis | X | X | X | | | | | X | | |
| Pharmacokinetic Methods | X | X | X | | | | | | | |
| Data Quality Assurance | X | | X | | | | | | | |
| Characteristics of a Well-Controlled Study | X | | X | | | | | | | |
| Amendments to the Protocol | X | | X | | | | | | | |
| Patient Information | X | | X | | | | | | | |
| Efficacy Data | X | | X | | | | | | | |
| Safety Data | X | | X | | | | | | | |

TABLE 2C

REPRESENTATIVE DOCUMENT TYPES AND TEST OBJECTS

| | | | | DOCUMENT TYPE | | | | | | |
|---|---|---|---|---|---|---|---|---|---|---|
| Object | IDB | Protocol | Full Report | Appendices | Tabulations | US Synopsis | EU Synopsis | Overview Table | ISE | ISS |
| | | | | TEST OBJECTS | | | | | | |
| RESULTS ORIENTED TEST OBJECTS | | | | | | | | | | |
| Protocol Variations | X | | X | | | | | | | |
| Disposition of Patients Entered | X | | X | L | L | | | | | |
| Reasons for Discontinuation | X | | X | L | L | | | | | |
| Demographic Information | X | | X | L | L | | | | | |
| Dosage Information | X | | X | L | L | | | | | |
| Concomitant Medications Results | X | | X | L | L | | | | | |
| Data Sets Analyzed | X | | X | L | L | | | | | |
| Patients Excluded | X | | X | L | L | | | | | |
| Summary of Efficacy Results | X | | X | L | L | X | X | | X | X |
| Efficacy Summary Table | X | | X | L | L | X | X | | X | |
| Efficacy Parameter 1 by Week | X | | X | L | L | | | | | |
| Subpopulation Analysis | X | | X | L | L | | | | | |
| Blood Level Information | X | | X | L | L | | | | | |
| Extent of Exposure | X | | X | L | L | | | | | |

TABLE 2D

REPRESENTATIVE DOCUMENT TYPES AND TEST OBJECTS

| | | | | DOCUMENT TYPE | | | | | | |
|---|---|---|---|---|---|---|---|---|---|---|
| Object | IDB | Protocol | Full Report | Appendices | Tabulations | US Synopsis | EU Synopsis | Overview Table | ISE | ISS |
| | | | | TEST OBJECTS | | | | | | |
| RESULTS ORIENTED TEST OBJECTS | | | | | | | | | | |
| Summary of Safety Results | X | | X | L | L | X | X | | | X |
| Summary of All Adverse Events | X | | X | L | L | | | | | |
| Treatment Emergent Signs and Symptoms | X | | X | L | L | | | | | |
| Deaths | X | | X | L | L | | | | | |
| Serious and Unexpected Adverse Reactions | X | | X | L | L | | | | | |
| Special Analysis of Adverse Events | X | | X | L | L | | | | | |
| Laboratory Tests Mean Changes from Baseline | X | | X | L | L | | | | | |
| Publications | X | | X | | | | | | | |
| Discussion | X | | X | | | | | | | |
| Conclusions | X | | X | | | X | X | X | X | X |
| Bibliography | X | | X | | | | | | | |
| List of Appendices | X | | X | X | | | | | | |
| List of Tabulations | X | | X | | X | | | | | |

In addition to specifying study details, text objects, and the arrangement thereof, the document templates may include standard plain text items that are usually included in the respective documents. For example, section headings may be included in the document templates for identifying the various sections of each document. At each location within the document template where a data object is to be retrieved from the clinical study data base, there is a control code identifying which object is to be retrieved.

A standard drug document that is generated by the drug document production system may pertain to a single study. Alternatively, a standard drug document may integrate data from several studies, for example, to produce a summary table of results across selected studies. When the user selects Document Generation 46 from the main menu 50, the DMUI provides a series of study selection menus 68 which allow the user to specify whether the desired document pertains to a single study or whether the desired document integrates data from more than one study, and to select the study(s) of interest. If a single-study document is selected, then the DMUI provides selection menus for selecting the study of interest. If a multiple-study document is selected, then the DMUI provides selection menus for selecting the multiple studies from which data is to be used in the document.

After the user has specified the study(s) that are to be the subject of the document, the DMUI provides a template selection menu 70 for allowing the user to select a document template. The template selections provided in menu 70 are selected from single-study templates or multiple-study templates in accordance with the options specified in menu 68. after the user has selected a document template, the DMUI provides an alternate text selection menu 72. The user then specifies on menu 72 which category of alternate text objects, if any, are to be used in the production of the document. For example, in the production of an FDA report the user may select an FDA report template in menu 70 and the FDA alternate text in menu 72. Once the alternate text, if any, has been selected in menu 72, the DMUI prompts the user for a filename to be assigned to the generated document. Then, the DMUI executes a document generation procedure 74 to produce the desired document and returns to the main menu 50.

Figure 7:
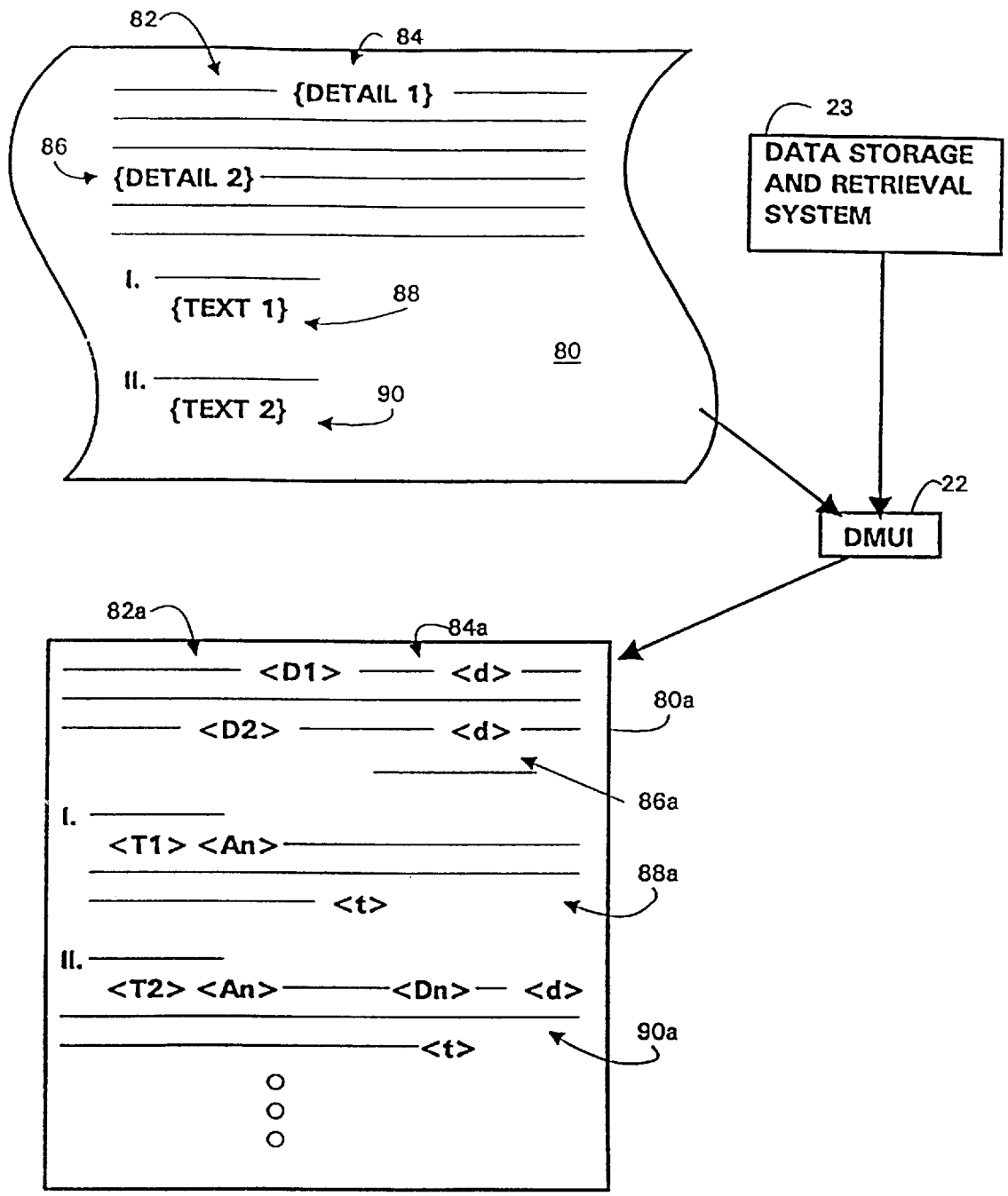
FIG. 7 is a diagram of a document generation process executed by the data management user interface of FIG. 3.

The document generation procedure 74 by which the DMUI generates a drug document on the basis of a document template and information stored within the clinical study database is effected as shown in FIG. 7. A document template 80 may include sections of plain text 82, detail codes 84 and 86, and text object codes 88 and 90. The detail code 84, shown as {DETAIL1}, indicates a location within the template where a specified detail is to be inserted when a document 80*a* is generated from the template 80. The detail code 84 identifies the detail which is to be inserted in template 80. The text object code 88, shown as {TEXT1}, indicates a location within the template 80 where a text object is to be inserted when the document 80*a* is generated, and identifies the text object which is to be inserted.

The DMUI retrieves the template 80 and then proceeds by copying the plain text 82 (represented in. FIG. 7 as solid lines) from the template 80 into document 80*a*, wherein the plain text 82 is reproduced as plain text 82*a*. When the DMUI encounters the detail code 84, {DETAIL1}, within the template 80, the DMUI retrieves the identified detail object from the appropriate detail file within the selected study entry of the clinical study database. The retrieved detail object is then placed into the document 80*a* as detail text 84*a*. When the detail text 84*a* is inserted into the document 80*a*, the DMUI also places a delimiter code, represented in FIG. 7 as <D1>, immediately preceding the detail text 84*a*. Additionally, the DMUI inserts a second delimiter code, represented in FIG. 7 as <d>, immediately after the detail text 84*a*. The first detail delimiter code, <D1>, includes one or more non-printed user-defined control codes that identify the start of an inserted detail and also specify the detail that was inserted into the document 80*a*. The second delimiter code, <d>, includes a non-printed user-defined control code that identifies the end of an inserted detail. These delimiter codes provide the ability to update the clinical study database on the basis of information contained within a drug document.

As the DMUI proceds in the generation of document 80*a*, the detail code 86, {DETAIL2}, is encountered within the template 80 and is then translated into the document 80*a*, via the use of the appropriate detail file, as detail text 86*a*. Within the document 80*a*, the detail text 86*a* is delimited by non-printed codes <D2> and <d> in a similar manner as has been described in connection with detail text 84*a*.

When the DMUI encounters the text object code 88, {TEXT1}, within the template 80, the DMUI consults the text object index of the selected study entry in order to locate the specified text object within the text object file. Alternatively, the DMUI may obtain, from the text object file, a further pointer to the desired text object, if the text object resides within another database accessible to the computer. If an alternate text category was selected by the user prior to commencing generation of document 80*a*, then the DMUI will obtain the location of the selected alternate text object from the corresponding alternate text pointer within the text object index. Then, the text object is retrieved from among the stored text objects, and is reproduced in document 80*a* as text 88*a*. In.addition to copying the text 88*a* into document 80*a*, the DMUI inserts a delimiter <T1> preceding the text 88*a* and a delimiter <t> after the text 88*a*. The delimiters <T1> and <t> serve to identify and mark the beginning and end of an inserted text object in the document 80*a* in a similar manner as has been described in connection with the detail delimiters. Additionally, a code <An> is inserted by the DMUI in association with the inserted text 88*a* in order to identify which category of alternate text, if any, was employed during the generation of that text object.

Text objects, such as 88 and 90, may be defined so as to contain embedded detail objects. When a text object is retrieved by the DMUI for placement into a generated document, the DMUI determines whether any embedded detail objects are contained within each such retrieved text object. For example, the document template 80 includes a text object code 90, {TEXT2}. When the text object code 90 is encountered during the generation of document 80*a*, the DMUI will consult the text object index of the selected study entry to obtain the location of the indicated text object and retrieve the text object from the appropriate text object file or remote database. Then, the DMUI will detect any detail codes within the retrieved text object and retrieve any required details. When the retrieved text object is reproduced within document 80*a* as text 90*a*, the embedded detail text is included within the reproduced text 90*a*. The embedded detail text, as reproduced within the generated document 80*a*, is also provided with appropriate detail delimiters <Dn> and <d>, as shown in FIG. 7, to mark and identify the embedded detail. The reproduced text 90*a* is also provided with appropriate text object delimiters <T2> and <t> to mark and identify the inserted text object.

When the DMUI has completed generating the document 80*a*, the document 80*a* can be provided to the word processor for any desired editing or refinement by the user. Additionally, the user may then instruct the word processor to operate the printer 51 for printing the generated document. As discussed herein, the electronic version of the generated document may include a variety of coded delimiters which are used by the DMUI for generating documents and for conversely updating the medical product database on the basis of delimited information within generated documents. Since non-printed, user-defined control codes may preferably be used to implement such delimiters, the delimiters are not reproduced in the printed documents.

TEMPLATE EDITING

From the main menu 50 of the DMUI, as shown in FIG. 3, the user may select the Template Editing option 47 in order to create new templates or to make changes to existing templates. Selection of the Template Editing option 47 activates the execution of a template editor 96. The template editor 96 includes a text editor for editing plain text that is to be included within a desired template. Additionally, the template editor includes appropriate function key assignments for specifying text format and layout options that are compatible with the word processor, and for inserting detail codes and text object codes into a template in the manner described in connection with template 80 of FIG. 7.

TOOLS

The tools option 48 of the main menu 50, as shown in FIG. 3, provides the user with access to other procedures associated with the management of clinical study data and the generation of documents. Upon selection of the tools option 48, the DMUI produces a menu 98 of tools including a "Location of Files" tool 98a, for setting default locations of database, document, template, and executable files of the document production system; an "Alternate Master List" tool 98b, for establishing categories of alternate text; and an "Update Study" tool 98c, for providing access to a procedure for entering study data into the clinical data base on the basis of information contained within a completed drug document.

Upon selection of the Alternate Master List option 98b from the tools menu 98, the DMUI provides the user with a list 100 of alternate text categories (i.e. FDA, EU, Company, etc.) from which the user may delete previously-defined categories or add new categories. When the user has made any desired changes in the list 100, such changes are reflected in the alternate text category list 40 that is stored within the data storage and retrieval system 23. Henceforth, when an alternate text category is desired by the user, the new alternate text category list will be provided to the user for selecting the desired category of alternate text. Additionally, any entries in the text object index will subsequently include pointers to any text objects defined to be within the newly-defined categories of alternate text.

Selection of the Update Study option 98c of the tools menu 98 initiates the display of one or more menus 99 for selecting the study to be updated and the document from which the study-is to be updated. Then, the DMUI initiates execution of a study update procedure 102. The study update procedure 102 provides the user with the ability to enter information into the clinical study database directly from the electronic version of a completed drug document. Such a feature is a useful alternative to specifying detail and text object information using the interactive forms of the DMUI.

For example, upon review of the generated document 80a of FIG. 7, an error may be found in one of the study details or in one of the text objects that was incorporated into the generated document 80a during the generation procedure. Furthermore, the identification of the data object in question may not be apparent to the person reviewing the document 80a. For example, the reviewer may desire to "mark-up" a printed document, in which case the text and detail delimiters are not present within the working copy of the document. In order to update the clinical study database to reflect any desired changes in a completed document, the user may first make or transfer the desired changes to the electronic version of the document using the word processor. Then, the user may invoke the clinical database update procedure 102 of the DMUI. The update procedure 102 then proceeds by locating detail delimiter codes and text object delimiter codes within the specified document and then copying the delimited data items into the appropriate locations within the study entry corresponding to the selected study within the clinical study database.

Referring to the completed document 80a of FIG. 7, the update procedure 102 will ignore the plain text 82a and will locate the detail delimiter <D1> indicating the start of the detail text 84a and identifying the type of detail so delimited. Then, the text 84a between the delimiters <D1> and <d> will be retrieved and placed into the detail file of the selected study at the location where the specified detail resides. The detail text 86a, delimited by the detail delimiters <D2> and <d>, is then also located and retrieved from the document 80a and placed into the appropriate detail file. When the text object delimiter <T1> is encountered, the text between <T1> and <t> is retrieved from the document 80a in order to update the text object file of the specified study. Additionally, the alternate text code <An> is retrieved and employed to properly update the text object index with a pointer to the new location of the encountered text object at the appropriate location in the text index pointer table for the specified category of alternate text.

When a text object is retrieved from a completed document and is placed into the text object file, the update procedure 102 also detects whether any details are embedded within the text object. For example, the text object 90a includes an embedded detail delimited by <Dn> and <d>. When the text object 90a is stored within the text object file, the corresponding detail reference code is substituted for the embedded detail, in the reverse manner to that used for placement of the embedded detail into the text object 90a when the document was generated.

As can be appreciated the use of non-printed code sequences within completed drug documents provides the ability for "top-down" creation or modification of the clinical study database, in addition to the "bottom-up" procedure of first entering data into the data base for subsequent generation of documents. For example, in the preferred embodiment it is possible to define so-called "keyboard macros" for manually inserting detail and text object delimiter codes into a document from within the word processor. Subsequently, the manually-inserted delimiter codes will be detected by the DMUI during the clinical study update procedure, and the data items delimited thereby will be placed into the appropriate locations within the clinical study database when the update procedure is invoked.

By providing drug documents in a format that is compatible with a standard word processing system, such documents are thereby compatible with various document compilation and publishing systems that are designed to further organize standard word processor files.

It will be recognized by those skilled in the art that changes or modifications may be made to the above-described embodiments without departing from the broad inventive concepts of the invention. For example, it is believed that the principles of the document production system described hereinabove will find wide applicability in the preparation of drug documents relating to studies of investigational or marketed drugs in areas such as nonclinical studies (e.g., pharmacology, toxicology, animal absorption, distribution, metabolism and excretion), human pharmacokinetics and bioavailability, microbiology, chemistry, manufacturing and controls, and other areas requiring work and documentation for regulatory purposes, in addition to having utility in connection with the composition and generation of clinical study documents as described above by way of example. It should therefore be understood that this invention is not limited to the particular embodiments described herein, but is intended to include all changes and modifications that are within the scope and spirit of the invention as set forth in the claims.

What is claimed is:

1. An apparatus for producing a document for regulatory review of a drug, comprising:
 a first electronic document template corresponding to a first regulatory authority for approving use of the drug within a first jurisdiction;
 a second electronic document template corresponding to a second regulatory authority for approving use of the drug within a second jurisdiction;
 a data storage system for storing said first and second templates and for storing a database for containing information pertaining to investigational studies of the drug;
 a computer connection with the data storage system, the computer configured to execute a data management interface integrated with a word processor, for storing and retrieving information in the database, and for composing said information to form the document on the basis of a selected one of said first and second templates; and
 wherein said data management interface is configured to generating a status report indicating a status of completion of said information stored in the database.

2. An apparatus for producing a document for regulatory review of a drug, comprising:
 a first electronic document template corresponding to a first regulatory authority for approving use of the drug within a first jurisdiction;
 a second electronic document template corresponding to a second regulatory authority for approving use of the drug within a second jurisdiction;
 a data storage system for storing said first and second templates and for storing a database for containing information pertaining to investigational studies of the drug;
 a computer connection with the data storage system, the computer configured to execute a data management interface integrated with a word processor, for storing and retrieving information in the database, and for composing said information to form the document on the basis of a selected one of said first and second templates; and
 wherein said database is configured to store alternative versions of a data item pertaining to the drug, and wherein the data management interface is arranged to select a corresponding one of said versions for inclusion in the document on the basis of the selected template.

3. The apparatus of claim 2 wherein the document is made available for manipulation within the word processor after composition, and wherein the data management interface is configured to update the information stored in the database on the basis of changes made to the document with the word processor.

4. The apparatus of claim 1 wherein said database is configured to store alternative versions of a data item pertaining to the drug, and wherein the data management interface is arranged to select a corresponding one of said versions for inclusion in the document on the basis of the selected template.

* * * * *